(12) United States Patent
Walsh et al.

(10) Patent No.: US 7,452,533 B2
(45) Date of Patent: Nov. 18, 2008

(54) ANTIMICROBIAL POLYMER CONJUGATE CONTAINING LYSOSTAPHIN AND POLYETHYLENE GLYCOL

(75) Inventors: Scott M. Walsh, Germantown, MD (US); Anjali G. Shah, North Potomac, MD (US); James J. Mond, Silver Spring, MD (US); Andrew Lees, Silver Spring, MD (US); Joseph J. Drabick, Silver Spring, MD (US)

(73) Assignee: Biosynexus Incorporated, Gaithersburg, MD (US)

( * ) Notice: Subject to any disclaimer, the term of this patent is extended or adjusted under 35 U.S.C. 154(b) by 428 days.

(21) Appl. No.: 10/403,223

(22) Filed: Mar. 26, 2003

(65) Prior Publication Data

US 2003/0215436 A1    Nov. 20, 2003

Related U.S. Application Data

(60) Provisional application No. 60/368,112, filed on Mar. 26, 2002.

(51) Int. Cl.
*A61K 38/48* (2006.01)
*A61K 38/51* (2006.01)
*C12N 11/08* (2006.01)

(52) U.S. Cl. .................................. 424/94.63; 435/180
(58) Field of Classification Search ........................ None
See application file for complete search history.

(56) References Cited

U.S. PATENT DOCUMENTS

| 4,179,337 | A |   | 12/1979 | Davis et al. ............... 435/181 |
|---|---|---|---|---|
| 4,261,973 | A |   | 4/1981 | Lee et al. .................... 424/78 |
| 4,301,144 | A |   | 11/1981 | Iwashita et al. ............. 424/78 |
| 4,732,863 | A |   | 3/1988 | Tomasi et al. .............. 436/547 |
| 4,847,325 | A |   | 7/1989 | Shadle et al. .............. 525/54.1 |
| 4,931,390 | A | * | 6/1990 | Recsei ........................ 435/183 |
| 5,760,026 | A |   | 6/1998 | Blackburn et al. .......... 514/192 |
| 5,783,178 | A | * | 7/1998 | Kabanov et al. ......... 424/78.31 |
| 6,028,051 | A |   | 2/2000 | Climo et al. .................... 514/2 |
| 6,315,996 | B1 |   | 11/2001 | O'Callaghan ............ 424/94.63 |
| 6,379,654 | B1 | * | 4/2002 | Gebreselassie et al. ........ 424/50 |
| 6,875,903 | B2 | * | 4/2005 | Bramley et al. ................ 800/3 |

FOREIGN PATENT DOCUMENTS

| EP | 154316 A2 | 9/1985 |
|---|---|---|
| EP | 154316 B1 | 9/1989 |
| JP | 403069665 A * | 3/1991 |
| JP | 403213516 A * | 9/1991 |
| JP | 411061569 A * | 3/1999 |
| WO | WO 90/15628 A1 | 12/1990 |
| WO | 01/04287 A1 | 7/2000 |
| WO | WO 01/10901 A2 | 2/2001 |

OTHER PUBLICATIONS

Zalipsky, "Functionalized Poly (ethylene glycol) for Preparation of Biologically Relevant Conjugates," *Bioconjugate Chem.*, 6, 150-165 (1995).
Gaertner et al., "Site-Specific Attachment of Functionalized Poly (ethylene glycol) to the Amino Terminus of Proteins," *Bioconjugate Chem.*, 7, 38-44 (1996).
Geoghegan et al., "Site-Directed Conjugation of Nonpeptide Groups to Peptides and Proteins via Periodate Oxidation of a 2-Amino Alcohol. Application to Modification at N-Terminal Serine," *Bioconj. Chem.*, 3 (2), 138-146 (1992).
Gaertner et al., "Chemo-enzymatic Backbone Engineering of Proteins," *J. Biol. Chem.*, 269 (10), 7224-7230 (1994).
Benhar et al., "*Pseudomonas* Exotoxin A Mutants," *J. Biol. Chem.*, 269 (18), 13398-13404 (1994).

* cited by examiner

*Primary Examiner*—David M Naff
(74) *Attorney, Agent, or Firm*—Casimir Jones S.C.

(57) ABSTRACT

Water-soluble polymer conjugates of antimicrobial agents retaining at least a portion of the antimicrobial activity of the agent, pharmaceutical compositions containing the polymer conjugates, and methods for treating microbial infections with the pharmaceutical compositions.

26 Claims, 7 Drawing Sheets

KILLING ASSAY WITH SHEARWATER 40K 1 AND 2-mer SAMPLES

LYSOSTAPHIN ACTIVITY IN BLOOD

KILLING ASSAY WITH SHEARWATER 30K 1 AND 2-mers

KILLING ASSAY WITH SHEARWATER 30 AND 40K 1-mer SAMPLES

SA KILLING WITH N-TERMINAL 30K 1-mer

ANTIMICROBIAL POLYMER CONJUGATE CONTAINING LYSOSTAPHIN AND POLYETHYLENE GLYCOL

CROSS-REFERENCE TO RELATED APPLICATION

The present application claims priority benefit under 35 U.S.C. §119(e) of U.S. Provisional Application Ser. No. 60/368,112 filed on Mar. 26, 2002, the disclosure of which is incorporated herein by reference.

FIELD OF THE INVENTION

The present invention relates to the conjugation of antimicrobial agents to water-soluble polymers to improve their clinical properties in terms of their pharmacokinetics, pharmacodynamics, and reduced immunogenicity. More specifically, the present invention relates to the conjugation of antimicrobial agents such as lysostaphin to poly(alkylene oxides), such as poly(ethylene glycol) (PEG).

BACKGROUND ART

A. Lysostaphin

Lysostaphin is a potent antimicrobial agent first identified in *Staphylococcus simulans* (formerly known as *S. staphylolyticus*). Lysostaphin is a bacterial endopeptidase capable of cleaving the specific cross-linking polyglycine bridges in the cell walls of staphylococci, and is therefore highly lethal thereto. Expressed in a single polypeptide chain, lysostaphin has a molecular weight of approximately 27 kDa.

The cell wall bridges of *Staphylococcus aureus*, a coagulase positive staphylococcus, contain a high proportion of glycine, therefore lysostaphin is particularly effective in lysing *S. aureus*. Lysostaphin has also demonstrated the ability to lyse *Staphylococcus epidermidis*.

*S. aureus* is a highly virulent human pathogen. It is the cause of a variety of human diseases, ranging from localized skin infections to life-threatening bacteremia and infections of vital organs. If not rapidly controlled, a *S. aureus* infection can spread quickly from the initial site of infection to other organs. Although the foci of infection may not be obvious, organs particularly susceptible to infection include the heart valves, kidneys, lungs, bones, meninges and the skin in burn patients.

Staphylococcal infections, such as those caused by *S. aureus*, are a significant cause of morbidity and mortality, particularly in settings such as hospitals, schools, and infirmaries. Patients particularly at risk include infants, the elderly, the immunocompromised, the immunosuppressed, and those with chronic conditions requiring frequent hospital stays.

Patients at greatest risk of acquiring staphylococcal infections, are those undergoing inpatient or outpatient surgery, in the Intensive Case Unit (ICU), on continuous hemodialysis, with HIV infection, with AIDS, burn victims, people with diminished natural immunity from treatments or disease, chronically ill or debilitated patients, geriatric populations, infants with immature immune systems, and people with intravascular devices.

U.S. Pat. No. 6,028,051 to Climo, et al., discloses a method for the treatment of staphylococcal disease. Relatively high doses of lysostaphin of at least 50 and preferably 100 milligrams of lysostaphin per kilogram of body weight are used for treatment. The relatively high doses of lysostaphin can be used in single dose treatments or multiple dose treatments. The lysostaphin analog can be used singularly or in combination with additional antibiotic agents. The '051 patent also discloses that the cloning and sequencing of the lysostaphin gene permits the isolation of variant forms of lysostaphin that can have properties similar to or different from those of wild type lysostaphin.

U.S. Pat. No. 6,315,996 to O'Callaghan, discloses a method for using lysostaphin as an effective antibiotic for topical treatment of staphylococcus corneal infections. U.S. Pat. No. 5,760,026 to Blackburn et al., discloses a method for using lysostaphin to eliminate and cure staphylococcal infections including the cure of mastitis by intramammary infusion. The method is directed to use in dairy cows.

However, small proteins (less than about 70 kDa), such as lysostaphin, have a relatively short half-life in blood after intravenous injection. Lysostaphin's rapid clearance from circulation may reduce its efficacy. At the same time, because it is derived from a bacterial species and therefore foreign to any mammalian species, lysostaphin is also a very immunogenic molecule, which further stimulates its clearance from the blood stream, especially in subjects that have had previous exposure to lysostaphin. Thus, lysostaphin's short circulating half-life cannot be effectively countered by increasing the amount or frequency of dosage. There exists a need for a means by which the circulating half-life of lysostaphin may be increased without increasing the amount or frequency of administration. It would even be more desirable to increase the circulating half-life of lysostaphin while at the same time reducing the amount or frequency of administration.

B. Polymer Conjugation

The conjunction of biologically active polypeptides with water-soluble polymers such as PEG is well-known. PEGylation is a process in which therapeutic polypeptides, such as enzymes and hormones, are coupled to one or more chains of polyethylene glycol to provide improved clinical properties in terms of pharmacokinetics, pharmacodynamics, and immunogenicity.

PEGylation can alter the characteristics of the polypeptide without affecting the ability of the parent molecule to function, thereby producing a physiologically active, reduced or non-immunogenic, water-soluble polypeptide composition. The polymer protects the polypeptide from loss of activity by reducing its clearance and susceptibility to enzymatic degradation, and the composition can be injected into the mammalian circulatory system with substantially no immunogenic response. PEGylation of enzymes and other polypeptides is described in detail in U.S. Pat. No. 4,179,337 to Davis et al., and in Zalipsky, "Functionalized Poly(ethylene glycol) for Preparation of Biologically Relevant Conjugates," *Bioconjugate Chem.*, 6, 150-165 (1995), both of which are incorporated by reference in their entirety herein.

Davis et al. disclose that polypeptides modified with PEG have dramatically reduced immunogenicity and antigenicity. PEG conjugates exhibit a wide range of solubilities and low toxicity, and have been shown to remain in the bloodstream considerably longer than the corresponding native compounds, yet are readily excreted. The conjugates have been shown not to interfere with the activity of other enzymes in the bloodstream or the conformation of polypeptides conjugated thereto.

PEG conjugation is typically accomplished by means of two commonly used types of linkages. One type of conjugation reacts a polypeptide amino group with a PEG molecule having an active carbonate, ester, aldehyde or tresylate group. Another type of conjugation reacts a polypeptide thiol group with a PEG molecule having an active vinyl sulfone, maleimide, haloacyl or thiorthopyridyl group, or other suitable electrophile. See, for example, Hermanson, *Bioconjugate Techniques* (Academic Press, San Diego 1966). One of the two terminal hydroxyls of the PEG is blocked by conversion to an alkoxy group when intermolecular cross-linking is not desired. A PEG molecule with one terminal methoxy group is referred to as mPEG.

The PEG molecule may be linear or branched, whereby PEG conjugates can be created by conjugating a single large PEG moiety to a single conjugation site, a single branched (but smaller) PEG moiety to a single conjugation site, or several small PEG moieties to multiple conjugation sites. When multiple conjugation sites are employed, this can result in the loss of bioactivity. In addition to PEG homopolymers, the polymer molecule can be copolymerized with other alkylene oxide moieties, or it can be another poly(alkylene oxide) homopolymer or copolymer.

A number of PEG-conjugates of therapeutic proteins have been developed exhibiting reduced immunogenicity and antigenicity and longer clearance times, while retaining a substantial portion of the protein's physiological activity. U.S. Pat. No. 4,261,973 describes the PEG conjugation of immunogenic allergen molecules to reduce the immunogenicity of the allergen. U.S. Pat. No. 4,301,144 discloses that the conjugation of PEG to hemoglobin increases the oxygen-carrying ability of the molecule. U.S. Pat. No. 4,732,863 discloses the conjugation of PEG to antibodies to reduce binding to Fc receptors. EP 154,316 and Katre et al., *Proc. Natl. Acad. Sci.*, 84, 1487 (1987) disclose PEG conjugated lymphokines such as IL-2. U.S. Pat. No. 4,847,325 discloses the selective conjugation of PEG to Colony Stimulating Factor-1 (CSF-1).

Interferon-β2 (INF-β2) has been conjugated without a loss of biological activity to the succinimidyl ester of a single, branched PEG molecule consisting of two 20 kDa monomethoxy PEG chains connected through a lysine molecule via urethane bonds. This PEG conjugate is targeted for the treatment of hepatitis C, by affecting host immunity and enhancing immune clearance of the virus. The administration of the INF-β2 can be reduced to once weekly from three-to-seven times a week, simplifying and improving patient compliance. In addition, serum levels are maintained with minimal peak-to-trough variation, toxicity is reduced, and efficacy is increased.

FDA approved PEGylated therapeutic polypeptides in clinical use include PEG conjugates of INF-β2, adenosine deaminase and asparaginase. PEGylated therapeutic polypeptides awaiting FDA approval include PEG conjugates of IL-2, IL-6 and Tumor Necrosis Factor. Each of these PEGylated products contains a polypeptide targeted at host cell activities or cancerous host cells, but not to microbes.EG conjugation has been disclosed of proteins such as alpha-1-proteinase inhibitor, uricase, superoxide dismutase, streptokinase, plasminogen activator, IgG, albumin, INFβ2, lipoprotein lipase, horseradish peroxidase, catalase and arginase. These proteins also do not target microbes. The PEG conjugation was reported to improve circulating half-life, decrease immunogenicity, increase solubility and, in general, increase efficacy, thereby permitting less frequent dosing. In most cases, the proteins required multiple PEG conjugations per molecule to improve in vivo performance, and the activity in vitro was significantly decreased by such modification.

WO 01/04287 published Jan. 18, 2002, discloses the use of mutagenic processes to modify polypeptides in general, and staphylokinase in particular, for improved performance of the PEG conjugate thereof.

There is otherwise no disclosure of a PEG conjugation of antimicrobial agents to optimize pharmacokinetics and pharmacodynamics. No reference discloses the conjugation of an antimicrobial agent, or a mutagenic modification thereof, with PEG so as to retain its biological activity while also increasing its circulating half-life and efficacy, and decreasing its antibody binding and toxicity.

SUMMARY OF THE INVENTION

The foregoing limitations are overcome by the present invention. The present invention provides for the polymer conjugation of antimicrobial agents to increase circulating half-life in vivo while retaining antimicrobial activity. The antimicrobial agent so modified may thus be used to treat or prevent infection at much reduced and/or less frequent dosages than the unmodified agent.

In addition to increasing circulating half-life while retaining antimicrobial activity, other advantages obtained by polymer conjugation include decreased antibody binding and increased killing, decreased immunogenicity and reduced binding to circulatory system surfaces, including the surfaces of man-made implant devices, both of which also increase circulating half-life, independent of the increase in circulating half-life typically obtained by the increase in molecular weight contributed by the polymer conjugate.

More specifically, the present invention provides water-soluble polymers conjugated to antimicrobial agents, so that at least a portion of the antimicrobial activity of the agent is retained. Antimicrobial agents suitable for use with the present invention include agents such as chemicals, peptides, proteins and lipopeptides that, upon contacting a microbe in a host, kill the microbe by any of a variety of techniques or inhibit microbial metabolism, without damaging host cells or tissues or eliciting a harmful host response. Antimicrobial enzymes are among the peptides and proteins that can be used.

While microbes are defined as including bacteria and fungi, staphylolytically active antimicrobial agents are desirable because of the aforementioned risks posed by staphylococcal infections. Among the staphylolytically active antimicrobial agents are proteins and peptides that function as staphylolytically active enzymes, including proteins capable of cleaving the cross-linked polyglycine bridges in the cell wall peptidoglycan of staphylococci, such as lysostaphin and lysostaphin analogues.

Water-soluble polymers include poly(alkylene oxides), polyoxyethylated polyols and poly(vinyl alcohols). Poly (alkylene oxides) include PEGs, poloxamers and poloxamines. The poly(alkylene oxide) is typically conjugated to a free amino group via an amide linkage formed from an active ester, such as the N-hydroxysuccinimide ester, of the poly (alkylene oxide). The poly(alkylene oxide) can be mPEG, either straight chained or branched, having a molecular weight between about five and about 100 kDa.

In another aspect, the invention relates to a method for the prophylactic or therapeutic treatment of a microbial infection in a mammal by administering to the mammal an effective amount of a pharmaceutical preparation containing the antimicrobial conjugate of the present invention in a pharmaceutically acceptable carrier. When the microbial infection is caused by a staphylococcus species with sufficient cell wall polyglycine cross-linking so that cells of the species are lysed by lysostaphin when contacted therewith, the lysostaphin or lysostaphin analogue conjugates of the present invention may be used. This embodiment of the method of the present invention is particularly effective for treating *Staph. aureus* infections. According to yet another aspect of the present invention, pharmaceutical compositions are provided for use in the inventive treatment method that contain the antimicrobial conjugates of the present invention in a pharmaceutically acceptable carrier.

The foregoing and other objects, features and advantages of the present invention are more readily apparent from the detailed description set forth below, taken in conjunction with the accompanying drawings.

DETAILED DESCRIPTION

Figure 1:
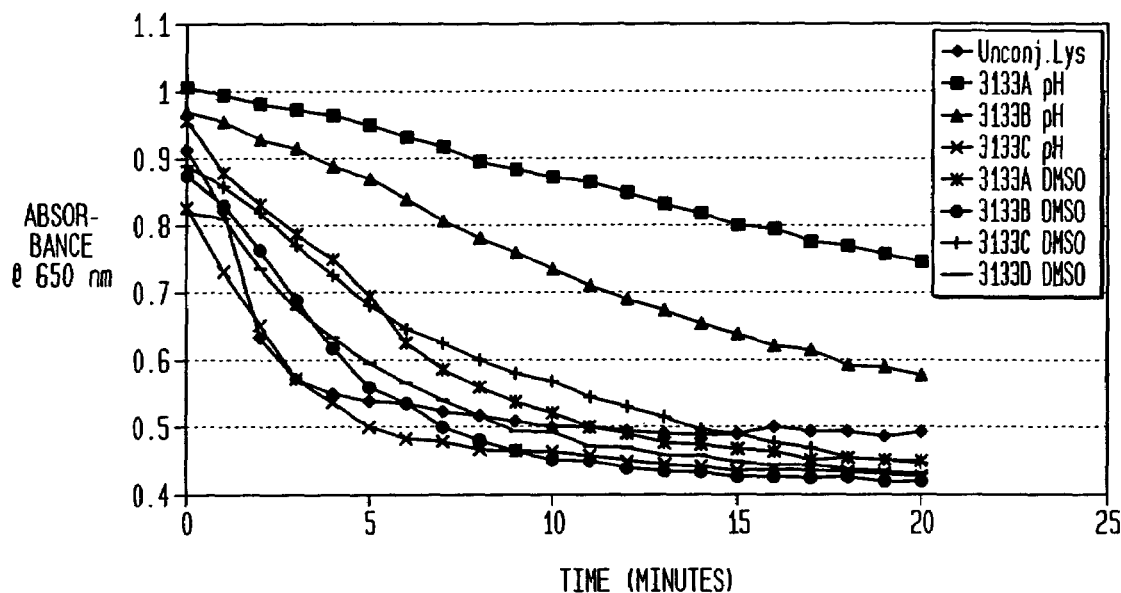
FIG. 1 depicts the lysis activity of lysostaphin conjugates according to the present invention in samples of heat-killed S. aureus type 5.

For purposes of the present invention, the term "antimicrobial agent" is defined as including any substances (chemical, protein, peptide or lipopeptide, including enzymes) that, upon contact such as in a host, kill microbes or inhibit microbe metabolism without damaging the surrounding environment, such as host cells or tissues, or upon contact with a host, elicit a harmful host response. This includes substances that would without polymer conjugation otherwise damage host cells or tissues or elicit a harmful response. The term "microbe" is defined as protists, which include bacteria and fungi.

The term "lysostaphin" is defined as including any enzyme, including lysostaphin (wild type), any lysostaphin mutant or variant, any recombinant, or related enzyme, or any synthetic version or fragment of lysostaphin that retains the proteolytic ability, in vivo and in vitro, to cleave the cross-linked polyglycine bridges in the cell wall peptidoglycan of staphylococci. Variants may be generated by post-translational processing of the protein (either by enzymes present in a producer strain or by means of enzymes or reagents introduced at any stage of the process) or by mutation of the structural gene. Mutations may include site deletion, insertion, domain removal and replacement mutations.

The term "lysostaphin analogue" is defined as including any form of lysostaphin that is not wild-type. The lysostaphin and lysostaphin analogues contemplated in the present invention may be recombinantly expressed from a cell culture or higher recombinant species such as a mouse or otherwise, expressed in mammalian cell hosts, insects, bacteria, yeast, reptiles, fungi, etc., or synthetically constructed. This would include the activity retaining synthetic construction including synthetic peptides and polypeptides or recombinant expression of portions of the lysostaphin polypeptide responsible for its activity against staphylococci alone, or as part of a larger protein or polypeptide, including chimeric proteins, containing the active site(s) of one or more other antimicrobial proteins or peptides that are active against staphylococci, or against one or more other microbe(s) or bacteria species to provide a broader spectrum of activity.

Lysostaphin is naturally produced by bacteria as a proenzyme that is cleaved to produce the full length form of lysostaphin. Recombinant or synthetically produced lysostaphin preparations can be used that contain only the fully active form of lysostaphin. The recombinant expression of homogenous lysostaphin, and homogenous fully active lysostaphin-containing compositions prepared from the expressed protein are disclosed in a U.S. Patent App. entitled, "Truncated Lysostaphin Molecule with Enhanced Staphylolytic Activity" filed by Jeffery Richard Stinson, Lioubov Grinberg, John Kokai-Kun, Andrew Lees and James Jacob Mond on Dec. 21, 2002, the disclosure of which is incorporated herein by reference in its entirety. The application claims priority from U.S. Provisional App. No. 60/341,804 filed Dec. 21, 2001.

Antimicrobial agents such as the lysostaphin and lysostaphin analogue proteins described above are conjugated to water-soluble polymers via free amino groups, either at lysine and arginine residues or a free amino group, if any, at the N-terminus. Other suitable antimicrobial agents include nisin, amphotericin-$\beta$, and the like. From a minimum of one up to about twelve water-soluble polymer molecules can be attached to each molecule of an antimicrobial agent. Because one object of the modification is to increase in vivo half life over the unconjugated antimicrobial agents with reduced immunogenicity, the number of conjugated polymers and the weight-average molecular weight of these molecules should be selected to provide a polymer conjugate of an antimicrobial agent with an apparent weight-average molecular weight from about 5 to 40 kDa, up to about 200 kDa.

The poly(alkylene oxides), when used, typically have weight-average molecular weights between about one and about 100 kDa, more typically between about two, three or four and about 50 kDa, and also between about five or ten and about 40 kDa, depending upon the number of conjugates per lysostaphin molecule. When conjugated to lysostaphin, from one to about ten poly(alkylene oxide) molecules per lysostaphin molecule can be used, with from one to about three or four being typically used, and one or two being more typical.

Lysostaphin compositions with mixed degrees of conjugation may also be used, or the lysostaphin conjugate may be fractionated so that a lysostaphin conjugate is obtained that essentially consists of a fraction of lysostaphin conjugated to essentially the same number of polymers. That is, essentially all lysostaphin in a fractionated sample is conjugated to one, two, three or more polymers, but not mixtures thereof.

When poly(alkylene oxides) are used, they may be straight chained or branched. Branched poly(alkylene oxides), such as branched PEG, because of their larger spatial volume, are believed to be less likely to penetrate protein crevasses, which are often the binding motifs and active sites of enzymes. Typical poly(alkylene oxides) consist of $C_2$-$C_4$ alkylene oxide groups, separately as homopolymers or in combination. This includes PEGs, poloxamers and poloxamines. The poly (alkylene oxides) can be substituted at one end with an alkyl group, or it may be unsubstituted. The alkyl group, when present, can be a $C_1$-$C_4$ alkyl group, and is typically a methyl group.

Suitable covalent modification reactions are well known and essentially conventional. Generally the process involves preparing an activated polymer and thereafter reacting the antimicrobial agent with the activated polymer. The reaction using N-hydroxysuccinimide activated mPEG (mPEG-NHS) described by Davis et al. can be used. MPEG-NHS is commercially available from Shearwater Corp. of Huntsville, Ala., now known as Nektar Therapeutics, AL.

Typically, the reaction is carried out in a buffer of pH about 7-8, frequently at about 10 mM Hepes pH 7.5, 100 mM NaCl. The reaction is carried out generally at 0° to about 25° C. for from about 20 minutes to about 12 hours, for example, for 25-35 minutes at about 20° C. or three hours at 4° C. Following the conjugation, the desired product is recovered and purified by column chromatography and the like.

The antimicrobial agent thus modified is then formulated as either an aqueous solution, semi-solid formulation, or dry preparation (e.g., lyophilized, crystalline or amorphous, with or without additional solutes for osmotic balance) for reconstitution. Formulations may be in, or reconstituted in, a non-toxic, stable, pharmaceutically acceptable, aqueous carrier medium, at a pH of about 3 to 8, typically 5 to 8, for administration by conventional protocols and regimes or in a semi-solid formulation such as a cream. Delivery can be via ophthalmic administration, intravenous (iv), intramuscular, subcutaneous or intraperitoneal routes or intrathecally or by inhalation or used to coat medical devices, catheters and implantable devices, or by direct installation into an infected site so as to permit blood and tissue levels in excess of the minimum inhibitory concentration (MIC) of the active agent to be attained and thus to effect a reduction in microbial titers in order to cure or to alleviate an infection. Further more, the antimicrobial agent can be formulated as a semi-solid formulation, such as a cream, that can be used in a topical or intranasal formulation.

Furthermore, the antimicrobial conjugate can be coadministered, simultaneously or alternating, with other antimicrobial agents so as to more effectively treat an infectious disease. Formulations may be in, or be reconstituted in, semi-solid formulations for topical, ophthalmic, or intranasal application, liquids suitable for ophthalmic administration, bolus iv or peripheral injection or by addition to a larger volume iv drip solution, or may be in, or reconstituted in, a larger volume to be administered by slow iv infusion. For example, the lysostaphin conjugate can be administered in conjunction with antibiotics that interfere with or inhibit cell wall synthesis, such as penicillins, such as nafcillin, and other β-lactam antibiotics, cephalosporins such as cephalothin, aminoglycosides, sulfonamides, antifolates, macrolides, quinolones, glycopepetides such as vancomycin and polypeptides. Or, the lysostaphin conjugate can be administered in conjunction with antibiotics that inhibit protein synthesis, for example aminoglycosides such as streptomycin, tetracyclines, and streptogramins. The lysostaphin conjugate may also be administered with monoclonal antibodies; other non-conjugated antibacterial enzymes such as lysostaphin, lysozyme, mutanolysin, and cellozyl muramidase; peptides such as defensins; and lantibiotics such as nisin; or any other lanthione-containing molecules, such as subtilin.

Agents to be coadministered with the lysostaphin conjugate may be formulated together with the lysostaphin conjugate as a fixed combination or may be used extemporaneously in whatever formulations are available and practical and by whatever routes of administration are known to provide adequate levels of these agents at the sites of infection.

Conjugates according to the present invention possess at least a portion of the anti-microbial activity of the corresponding non-conjugated antimicrobial agent. It is not essential that complete (or full) activity be retained because increased dosages at less frequent intervals can be given due to the decreased immunogenicity and increased circulating half-life produced by PEGylation. Conjugates that retain at least 10% of the activity of the non-conjugated antimicrobial agent are preferred, with conjugates that retain at least 15%, 20%, 25%, 30%, 40%, etc., of the non-conjugated antimicrobial agent activity are more progressively preferred.

Suitable dosages and regimes of the lysostaphin conjugate may vary with the severity of the infection and the sensitivity of the infecting organism and, in the case of combination therapy, may depend on the particular anti-staphylococcal agent(s) used in combination. Dosages may range from about 0.05 to about 100 mg/kg/day, preferably from about 1 to about 40 mg/kg/day, given as single or divided doses, or given by continuous infusion.

The present invention is further illustrated by the following examples that teach those of ordinary skill in the art how to practice the invention. The following examples are merely illustrative of the invention and disclose various beneficial properties of certain embodiments of the invention. The following examples should not be construed as limiting the invention as claimed.

EXAMPLES

Materials

As an example of an antimicrobial agent, lysostaphin was employed for these studies, which can be repeated with essentially any antimicrobial agent, as the term is defined by the present specification. Lysostaphin (Ambicin L) was obtained from AMBI, Inc. (now Nutrition 21). The mPEG2-NHS esters, 10 and 40 kDa were purchased from Shearwater Corporation (Huntsville, Ala.) (now Nektar Therapeutics, AL). Sodium Borate, DMSO, bovine serum albumin, and extravidin-HRP were purchased from Sigma Chemical Co. (St. Louis, Mo.). Glycine was purchased from EM Science (Gibbstown, N.J.). The NuPage Electrophoresis System and Colloidal Blue stain were purchased from Invitrogen (Carlsbad, Calif.). Sephacryl S-100HR and HiTrap SP FF were purchased from Amersham-Pharmacia (Piscataway, N.J.). Tryptic Soy Broth, TSB, and Cation-Adjusted Mueller Hinton Broth, CAMHB, were purchased from Becton Dickinson (Sparks, Md.). TMB Microwell and 450 STOP Reagent were purchased from BioFX (Owings Mills, Md.).

Example 1

Study of PEGylated Lysostaphin

Lysostaphin PEGylation

Lysostaphin at 0.27, 1, or 5 mg/mL was dissolved in either 0.2M borate buffer (pH 8.5) or DMSO. The mPEG2-NHS esters were prepared in DMSO and added to the lysostaphin solution in molar excess at ratios of 40, 20, 10, 5 or 2.5:1. PEGylation was performed with three different buffer conditions, all at room temperature for 1, 2, or 3 hours: borate buffer (with <10% DMSO contributed by adding PEG), 50% borate/50% DMSO, and 100% DMSO. All reactions were quenched by added glycine to 25 mM and vortexing.

PEG conjugation to lysostaphin was evaluated by SDS-PAGE with the NuPage Electrophoresis System. Non-reduced samples (300ng) were run on a Novex 4-12% Bis-Tris gel at 115V and stained with colloidal blue. PEGylated lysostaphin was separated from unreached lysostaphin by running the reaction mixture over a Sephacryl S-100HR™ column. Purified PEG-lysostaphin was concentrated and saved for activity assays.

Alternatively, unconjugated lysostaphin was removed from the sample by ion-exchange chromatography. Lysostaphin, but not PEG-lysostaphin, was bound onto a HiTrap SP FF column in 50 mM sodium phosphate buffer, pH 7.0. The column was washed with the same buffer until the OD280 of the eluate was reduced to background levels. Bound lysostaphin was then removed, and the column regenerated by washing with 50 mM sodium phosphate plus 1 M NaCl, pH 7.0. This process was repeated several times until the PEG-lysostaphin fraction (unbound) was at least 99% pure of unconjugated lysostaphin.

In Vitro Activity of PEG-Lysostaphin

Lysostaphin's ability to lyse *staphylococcus aureus* type-5 (SA5) was determined by measuring the drop in absorbance at 650 nm of a solution containing heat-killed SA5 (HKSA5). HKSA5 was prepared by incubating live bacteria at 62° C. for 2 hours and then diluted such that the initial absorbance was about 1. Lysostaphin was then added at a concentration of 32 µg/mL and absorbance readings were taken every 60 seconds for 20 minutes. Clearance of live SA5 cultures were measured by adding lysostaphin from 0 to 10 µg/mL to an SA5 suspension in PBS (% T=40). The samples were incubated at 37° C. for 1 hour and then spread onto blood agar plates. After overnight culture at 37° C., colonies were counted and compared to untreated samples.

The minimum inhibitory concentration (MIC) of the conjugated lysostaphin was determined against SA5. After an overnight culture of SA5 in TSB, the bacteria was diluted to % T=80. 100 µL of growth media (CAMHB+1% BSA+0 to 32 µg lysostaphin) was added to each well of a 96-well culture plate. 5 µL of SA5 was added to each well and the plate incubated at 37° µC. and 200 rpm for 24 hours. The absorbance at 650 nm was read and the MIC defined as the last well where there was no SA5 growth.

Anti-Lysostaphin Binding Activity

A lysostaphin capture ELISA was performed to determine if PEGylated lysostaphin shields the protein from antibody binding. 96-well microtiter plates were coated with a polyclonal rabbit anti-lysostaphin antibody overnight. The wells were blocked with 1% BSA followed by incubation with the lysostaphin samples in PBS/0.5% Tween 20 plus 0.1% BSA. Lysostaphin binding was detected with biotin-labeled, polyclonal rabbit anti-lysostaphin followed by extravidin-HRP incubation and TMB colorimetric detection. The plates were measured at an absorbance of 450 nm in a SpectraMAX Plus plate reader (Molecular Devices; Sunnyvale, Calif.).

Serum Pharmacokinetics of PEG-Lysostaphin

CF1 mice were injected in the tail vein with S-100HR purified PEG-lysostaphin at a dose of 0.8 or 0.2 mg (4 or 1 mg/mL in 0.2 mL PBS). Control mice were injected with 0.8 mg of unconjugated lysostaphin. Blood was collected by orbital eye bleeding at 1, 4, 7, and 24 hours post-administration. The blood was incubated at 37° C. for 30 minutes followed by 4° C. for 30 minutes. Serum was then separated by centrifugation at 1000 g for 10 minutes. The serum concentration of lysostaphin was determined by ELISA as described above.

Results

Lysostaphin has a high net charge of +10.53 at pH 7 due to a large number of lysine (16) and arginine (6) residues. The primary amine groups of the side chains of these lysines are ideal targets to covalently link PEG that has been activated with N-hydroxysuccinimide. Branched PEG's were chosen because their larger spatial volume makes them less likely to penetrate protein crevasses, which are often the binding motifs and active sites of enzymes.

The reaction conditions can be manipulated to create a PEGylated lysostaphin molecule that has an optimal balance between enzyme activity and enhanced properties such as reduced immunogenicity, decreased antibody binding and toxicityand increased serum half-life and efficacy. Unique reaction groups may be added to lysostaphin in order to conjugate PEG in a number controlled and site specific matter. Creating sulfhydryl groups would be one way to achieve this goal because lysostaphin does not contain any cysteine residues. Another way to achieve this goal would be to introduce thiol groups into the protein by introducing the thiol-containing amino acid cysteine into the amino acid sequence of the protein through genetic engineering.

Enzyme Killing Activity on SA5

Figure 2:
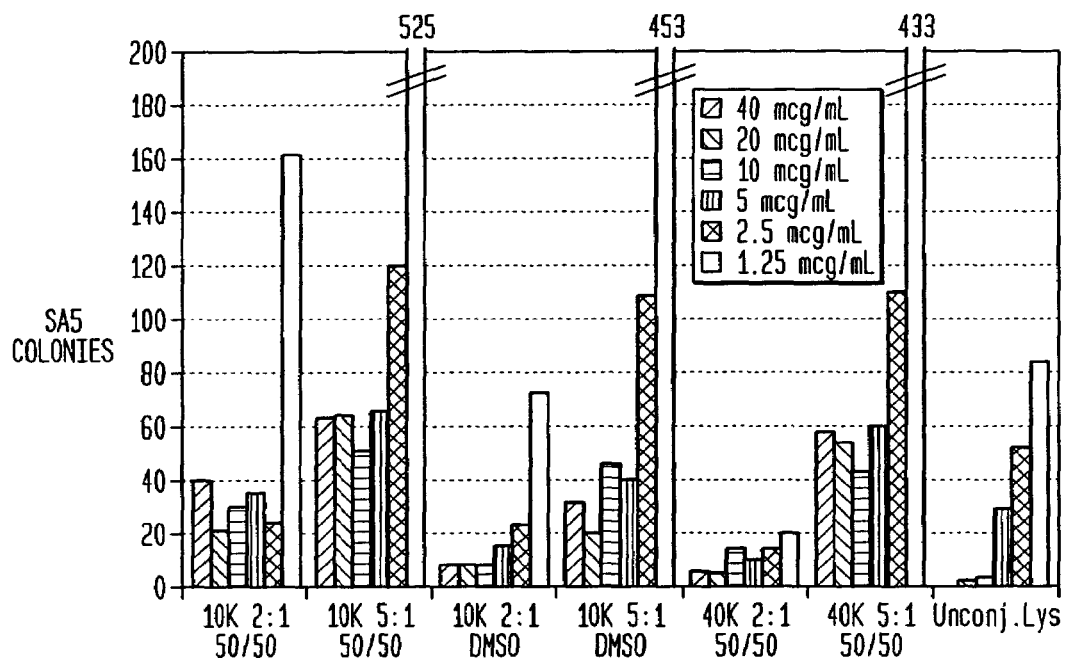
FIG. 2 depicts the killing activity of lysostaphin conjugates according to the present invention in a high innoculum of live S. aureus type 5.

The in vitro killing activity of five PEGylated lysostaphin samples was tested by measuring lysis of heat-killed SA5 (FIG. 1) and killing of live SA5 (FIG. 2). In FIG. 1, lysostaphin conjugated to 10 kDa PEG is represented in lines 3133A-B pH and 3133A-DMSO. The pH designation indicates PEGylation reactions that took place in aqueous solution. The DMSO designation designates PEGylation reactions that were performed in 100% DMSO. All samples were positive for enzyme activity. A reduction in activity with increasing degrees of PEGylation suggests that the 10 kDa PEG is small enough to gain access to lysostaphin's active site or its peptido-glycan binding domain, thus reducing its enzyme activity. In contrast, no reduction in enzyme activity was observed with the 40 kDa PEG samples despite the fact that no size separation was performed on these samples. This implies that the highly PEGylated forms retain similar activity to lightly conjugated forms and indicates that the 40 kDa PEG cannot easily access sites important for enzyme function.

The ability to kill live SA5 in vitro was tested with decreasing concentrations of PEGylated lysostaphin (FIG. 2). As was observed for the heat-killed assay, higher degrees of PEG conjugation reduced lysostaphin activity and the 40 KDa conjugate retained more activity than the 10 kDa form. However, new properties of PEG-lysostaphin emerged that were not apparent in the heat-killed assay. The killing curve for unconjugated lysostaphin shows the titration of response with decreasing enzyme concentrations, but all of the PEGylated enzymes appear to have a flat response over the first four dilutions before finally titrating upward. In particular, the 40 kDa PEG at a 2:1 ratio maintains greater killing over the lowest three concentrations, compared to unconjugated lysostaphin, but is comparatively less active at the three highest concentrations. This finding indicates that PEGylated lysostaphin has modified activity or metabolism. PEG may shield the enzyme from degradative proteases that are released from the bacteria as they are killed, thus enabling lysostaphin to remain active for a longer period of time at lower concentrations. Another possibility is that PEG conjugated onto lysostaphin may alter the enzymes interaction with the bacterial cell wall. Reduced binding affinity to its cell wall docking site, while still enabling peptidoglycan cleavage, would result in quicker enzyme release and speed the recycling of lysostaphin for the next round of cleavage. Either of these explanations, and others yet undiscovered, could explain the observed response and each is equally encouraging for the prospect of creating a PEGylated form of lysostaphin that is superior to the native drug.

Inhibition of SA5 Growth

The minimum inhibitory concentration (MIC) is a quantitative measure of a drug's activity that is typically used to examine levels of resistance in different bacterial strains. This was used this assay against a single strain of SA5 to measure loss of drug activity upon lysostaphin PEGylation, as shown in Table 1. Several formulations retained high levels of activity although none were as high as un-conjugated lysostaphin. The pattern of activity observed with the different PEG-lysostaphin species is consistent with that observed in the previous killing assays. The more lightly PEGylated lysostaphin retained greater activity than highly conjugated forms and under the same reaction conditions, the 40 kDa PEG conjugate was eight times more active than the 10 kDa PEG conjugate.

TABLE 1

MIC of PEGylated Lysostaphin Against SA5

| TYPE OF LYSOSTAPHIN | MIC ($\mu$g/mL) |
|---|---|
| 10K 2:1 50/50 | 4 |
| 10K 5:1 50/50 | >32 |
| 10K 2:1 DMSO | 2 |
| 10K 5:1 DMSO | 16 |
| 40K 2:1 50/50 | 0.5 |
| 40K 2:1 50/50 | >32 |
| Unconjugated | 0.13 |

Both of these findings support the conclusion that low degrees of PEGylation result in an active enzyme and that the bulkier 40 kDa PEG lysostaphin conjugate was more active than the 10 kDa conjugate. The small loss in activity observed with the 2:1 PEG ratios is an acceptable trade-off for the increased serum half-life of this conjugate and its reduced immunogenicity. The potential benefits of these conjugates include reduced dosing frequency, reduced ability to induce antibody, retention of activity in patients with anti-lysostaphin lysostaphin antibodies, and reduced toxicity associated with immunogenic reactions.

Anti-Lysostaphin Antibody Activity for PEGylated Lysostaphin

Figure 3:
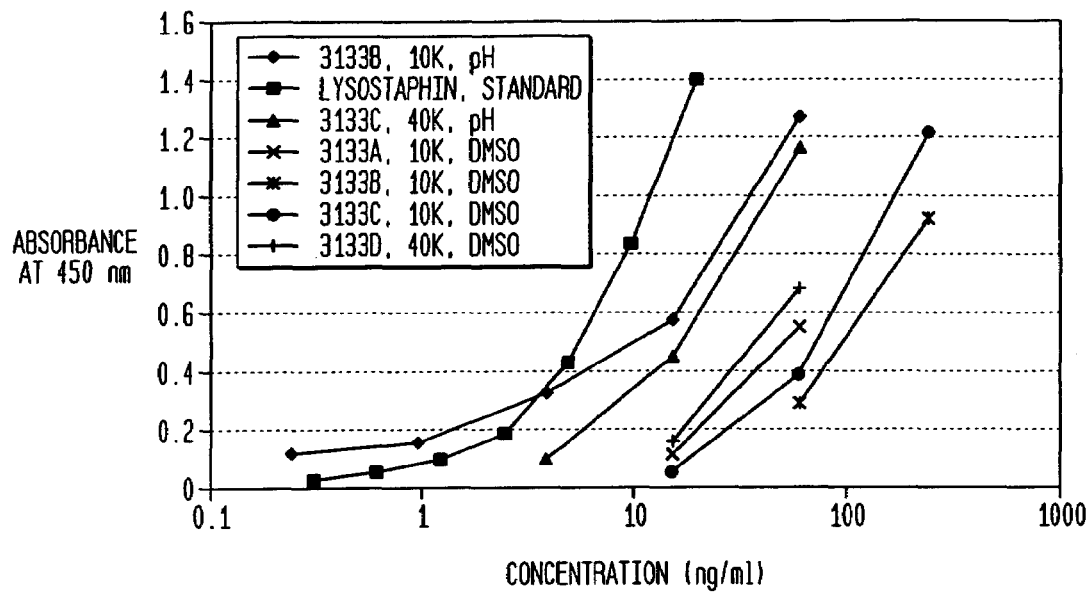
FIG. 3 is a lysostaphin-capture immunoassay depicting the ability of PEG to shield lysostaphin from antibodies.

The ability of PEG to shield lysostaphin from antibodies was tested in vitro with a lysostaphin-capture immunoassay (FIG. 3). Unconjugated lysostaphin shows a standard response from 0.3 ng/mL to 20 ng/mL. A heterogeneous response is seen with the binding of PEG-lysostaphin to anti-lysostaphin antibody, but all bind less efficiently than unconjugated lysostaphin. The best shielding observed resulted in a greater than 10-fold reduction in antibody affinity to the PEGylated lysostaphin. This assay environment is different than binding in mucosal surfaces or flowing serum, but it does prove that PEG conjugation onto the surface of lysostaphin can at least partially shield the enzyme from antibody binding. There does not appear to be any correlation between enzyme activity and reduced antibody binding, but differences in antibody binding to the 40 kDa and 10 kDa conjugates may be explained by differing degrees of PEGylation. In general, fewer PEG molecules are attached to lysostaphin for the 40 kDa PEG, so it may have a more open structure that does not exclude antibodies as well as the 10 kDa form, which may also explain why the 40 kDa conjugate has better activity. Nevertheless, antibody activity for the 40 kDa conjugate is reduced compared to unconjugated lysostaphin.

Prolonged Serum Half-Life of PEGylated Lysostaphin

Figure 4:
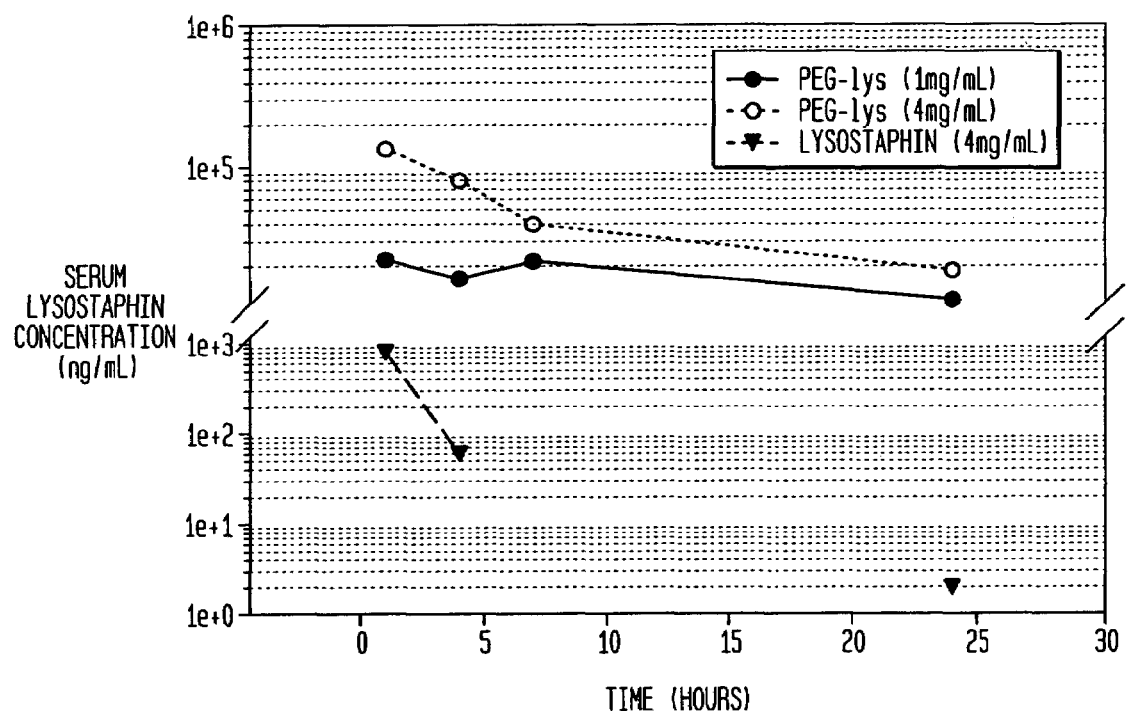
FIG. 4 depicts the serum concentrations and half-life of one lysostaphin conjugate at two different concentrations according to the present invention, in comparison to unconjugated lysostaphin.

Conjugation of PEG onto protein drugs enables them to avoid the normal clearance mechanisms of the body and thereby leads to increased serum half-life of the drug. The pharmacokinetic profile of lysostaphin with a low degree of PEG modification (1 to 4 PEG's per lysostaphin) was determined in mice and compared to clearance of unconjugated lysostaphin (FIG. 4). Two enhancements because of PEGylation are apparent from the graph: (1) the half-life of lysostaphin has been dramatically increased and (2) the total serum concentration achieved is much greater than for unconjugated lysostaphin. The serum concentration of the PEG-lysostaphin conjugates drops by only two- to ten-fold over 24 hours whereas unconjugated lysostaphin falls by nearly 500-fold over the same time period. Such a prolonged retention of lysostaphin should reduce the dosing frequency needed to remain above therapeutically effective concentrations of the drug.

Maintaining these levels of lysostaphin for longer periods of time may also result in more rapid clearance of bacterial infections and decrease the probability that lysostaphin resistance will emerge. Total serum concentrations were also much greater with the PEG-lysostaphin conjugates. At 24 hours post-administration, serum concentrations of PEG-lysostaphin were more than 10 times the concentration of native lysostaphin at just 1 hour post-administration, even when the initial PEG-lysostaphin dose was ¼ that of unconjugated lysostaphin. This result suggests that a much lower dose of PEG-lysostaphin may be used to achieve the same or better clinical benefit as conjugated lysostaphin, which could result in lower cost of therapy and minimize potential toxic or allergic reactions to the drug. The foregoing Example thus illustrates the increased activity and prolonged circulating half-life of the lysostaphin conjugates of the present invention.

Example 2

Fractionation of 40 kD PEG Lysostaphin Conjugates

Fractionation of the various 40 kD PEG—lysostaphin conjugate species of Example 1 was performed by ion-exchange chromatography as a means to test enzyme activity as a function of PEG conjugation number. Although perfect resolution was not achieved, fractions tended to be enriched in just one specific band. The mono-PEGylated form was purified to greater than 99% 1-mer, while the di-PEGylated form was purified to 93% 2-mer with the remainder contributed mostly by the 1-mer, as determined by size-exclusion chromatography HPLC.

Figure 5:
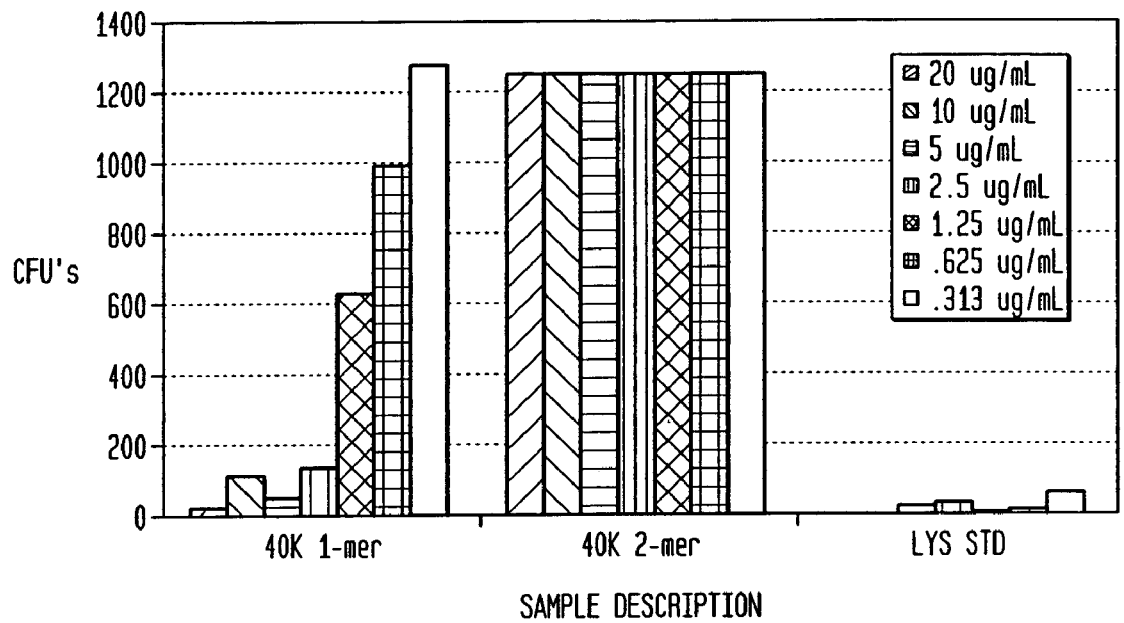
FIG. 5 depicts the S. aureus type 5 killing activity in saline of lysostaphin conjugates according to the present invention.

Killing Assay for Activity: The ability of lysostaphin to kill SA in saline was tested with varying concentrations of the enzyme. The bacteria were streaked onto blood agar plates after a 1-2 hour incubation with lysostaphin and surviving colonies were counted the next day. The data is reported in FIG. 5 as surviving colonies of SA so that the lower value on the graph, the more effective the killing of SA by lysostaphin. The 1-mer has greater activity than the 2-mer, but both have significantly reduced activity compared to unconjugated lysostaphin.

Figure 6:
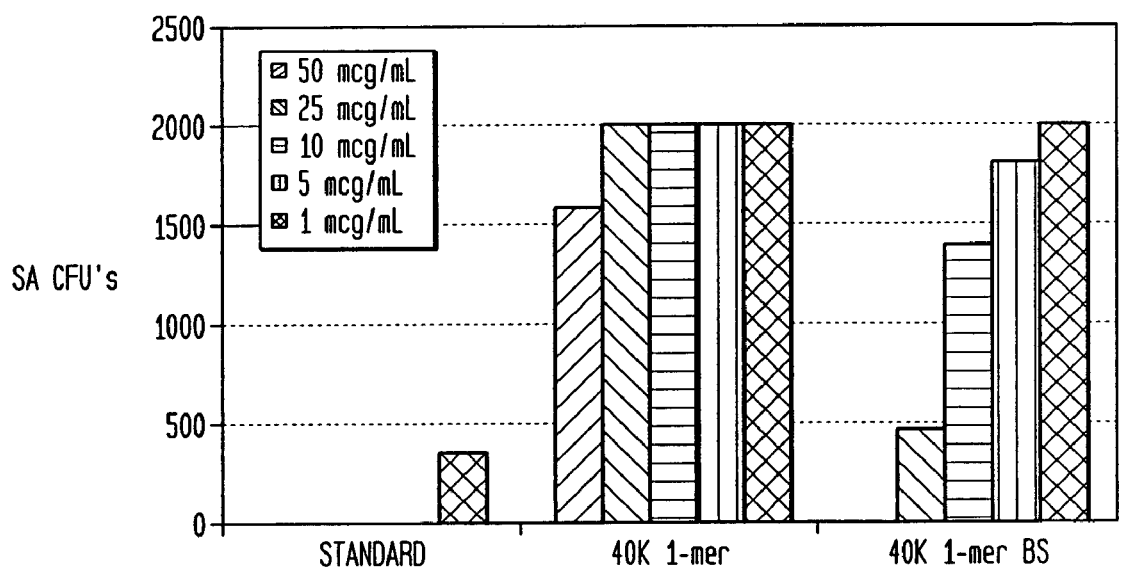
FIG. 6 depicts the S. aureus type 5 killing activity in blood of lysostaphin conjugates according to the present invention.

Killing Activity in Blood: The ability of lysostaphin to kill SA in whole, heparinized human blood was tested with varying concentrations of the enzyme. The bacteria were streaked onto blood agar plates after a 1-2 hour incubation with lysostaphin and surviving colonies were counted the next day. The data is reported in FIG. 6 as surviving colonies of SA so that the lower value on the graph, the more effective the killing of SA by lysostaphin. The 40 k 1-mer BS was the Example 1 conjugate made with 50% DMSO. The activity of the 40 k 1-mer is reduced as was observed in the killing assay performed in saline, but the reduction in activity appears to be even greater in blood than in saline.

There are two possible explanations for the loss of activity with the 2-mer. Although there may be as many as 10 lysine residues available for PEG conjugation onto lysostaphin, each will have a different reactivity, and it is likely that only one or two lysine residues are preferentially PEGylated for a given reaction condition. The preferred site for conjugation of the first PEG chain might lie in a region that is not critical for enzyme function and may explain why there is little loss inactivity for the 1-mer. However, the next-most-preferred lysine for PEGylation may reside in or near the active or cell wall binding sites of lysostaphin, and attachment of PEG to these regions may seriously disrupt enzyme function.

Another possible explanation for the loss of activity with the 2-mer relates to the increased spatial volume of lysostaphin due to PEGylation. Lysostaphin does not act on a soluble, diffusible substrate but rather must be able to penetrate the thick, solid peptidoglycan scaffold of the bacterial cell wall. Each successive addition of PEG raises the molecular weight of lysostaphin, and the increase in spatial volume from the 1-mer to the 2-mer may hinder enzyme access to the pentaglycine cross bridges in the cell wall, thus eliminating its killing activity.

Figure 7:
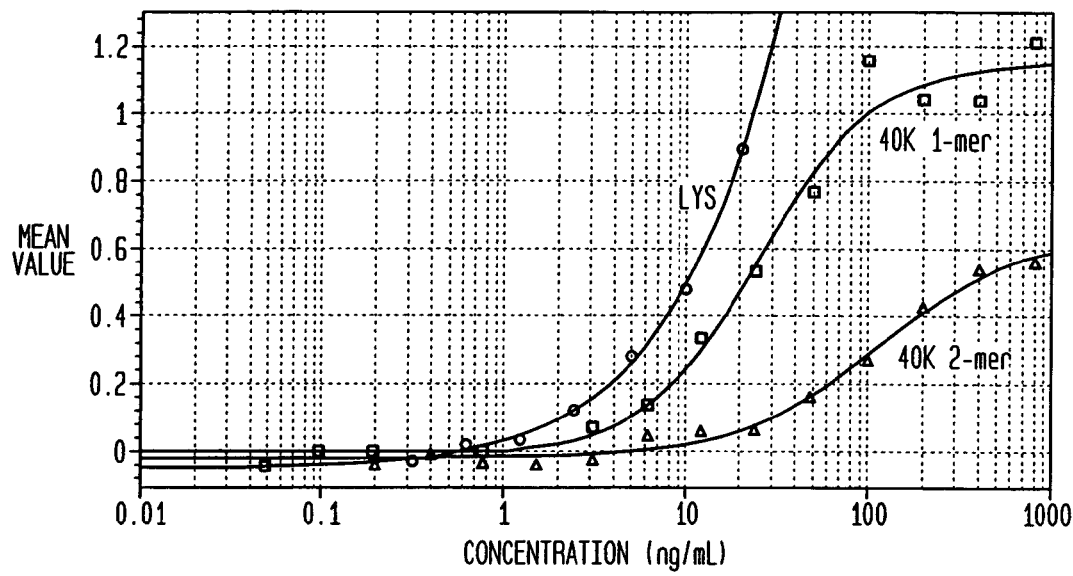
FIG. 7 is an ELISA depicting the reactivity of anti-lysostaphin antibodies to lysostaphin conjugates according to the present invention.

Antibody Reactivity: Reactivity of anti-lysostaphin antibodies to PEGylated lysostaphin was measured by ELISA (FIG. 7): 96-well plates were coated with a polyclonal anti-lysostaphin antibody (Ab) and then incubated with lysostaphin. Bound lysostaphin was then detected with a polyclonal, HRP-labeled, anti-lysostaphin Ab. The binding level of lysostaphin to these antibodies (Mean Value on y-axis of graph) was determined as a function of enzyme concentration. Both PEG conjugates have reduced Ab binding activity compared to unconjugated lysostaphin, but the 2-mer was much less reactive than the 1-mer.

Example 3

Fractionation of 30 kD PEG-Lysostaphin Conjugates

Figure 8:
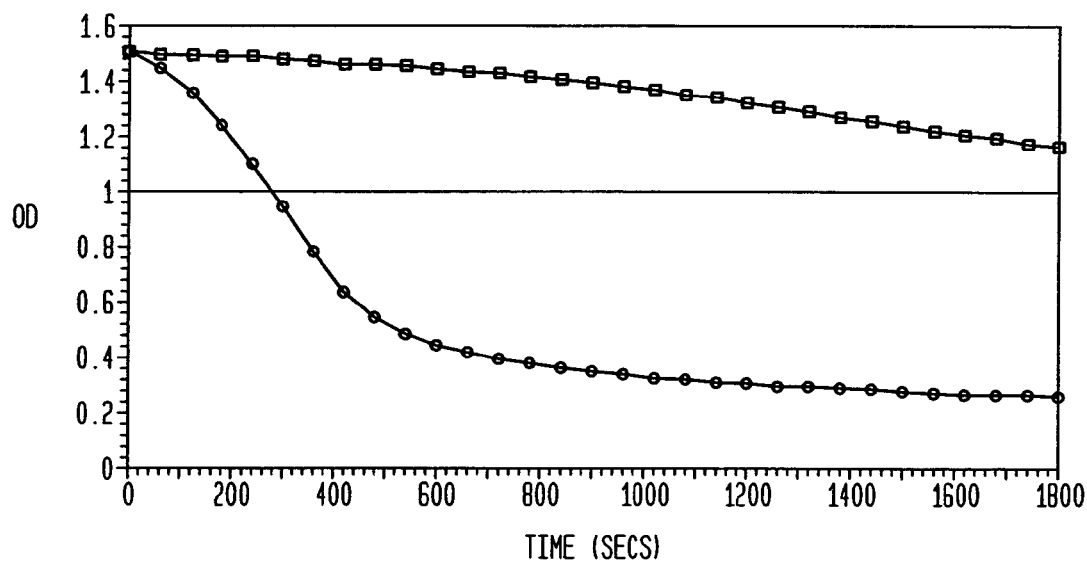
FIG. 8 depicts the lysis activity of lysostaphin conjugates according to another aspect of the present invention in samples of heat-killed S. aureus type 5.
Figure 9:
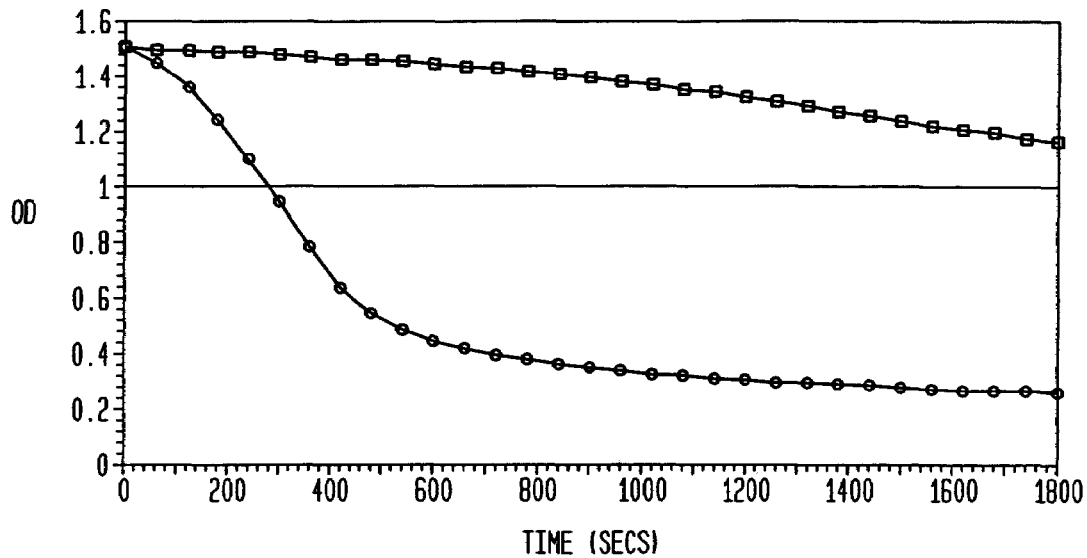
FIG. 9 depicts the lysis activity of lysostaphin conjugates according to yet another aspect of the present invention in samples of heat-killed S. aureus type 5.

Example 2 was repeated substituting 30 kD PEG for 40 kD PEG and 1-mers and 2-mers of mPEG 30 kD lysostaphin conjugates were isolated in separate fractions having the following properties:

OD drop assay: The OD at 280 nm of a high innoclulum of S. aureus (SA, about $10^9$/mL) in saline is monitored over time. When bacteria are lysed, the OD drops and thus is a measure of lysostaphin activity. The faster the OD drops, the greater the enzyme activity. A typical standard takes 6-7 minutes to reach 50% of starting OD. The 1-mer has greater activity than the 2-mer, but both have significantly reduced activity compared to unconjugated lysostaphin (FIGS. 8 and 9).

Figure 10:
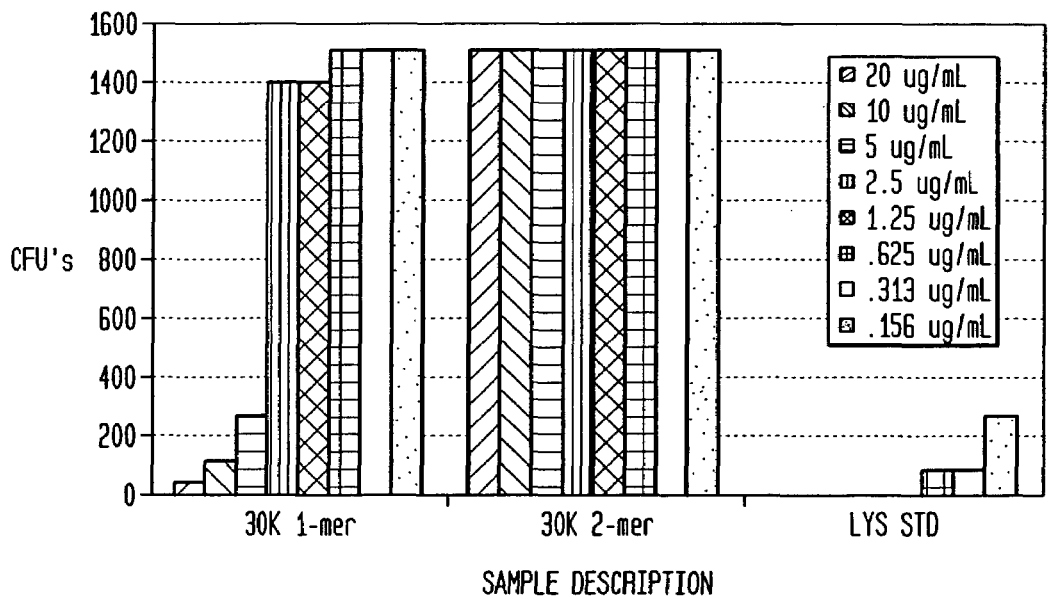
FIG. 10 depicts the S. aureus type 5 killing activity in saline of lysostaphin conjugates according to another aspect of the present invention.

Killing Assay for Activity: The ability of lysostaphin to kill SA in saline was tested with varying concentrations of the enzyme. The bacteria were streaked onto blood agar plates after a 1-2 hour incubation with lysostaphin and surviving colonies were counted the next day. The data is reported as surviving colonies of SA so that the lower value on the graph, the more effective the killing of SA by lysostaphin. The 1-mer has greater activity than the 2-mer, but both have significantly reduced activity compared to unconjugated lysostaphin (FIG. 10).

Figure 11:
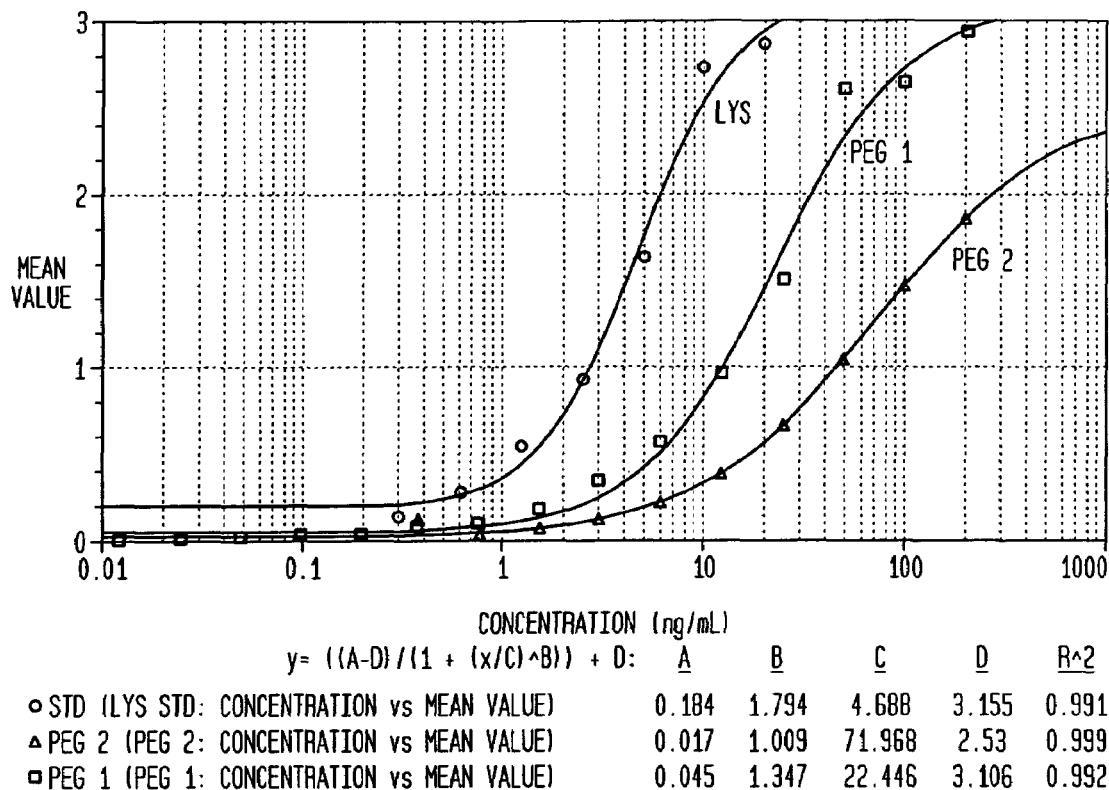
FIG. 11 is an ELISA depicting the reactivity of anti-lysostaphin antibodies to lysostaphin conjugates according to another aspect of the present invention.

Antibody Reactivity: Reactivity of anti-lysostaphin antibodies to PEGylated lysostaphin was measured by ELISA. 96-well plates were coated with a polyclonal anti-lysostaphin Ab and then incubated with lysostaphin. Bound lysostaphin was then detected with a polyclonal, HRP-labeled anti-lysostaphin Ab. The binding level of lysostaphin to these antibodies (Mean Value on y-axis of graph) was determined as a function of enzyme concentration. The 1-mer has about 7× less Ab binding activity and the 2-mer has about 70× less Ab binding activity compared to unconjugated lysostaphin (FIG. 11).

Figure 12:
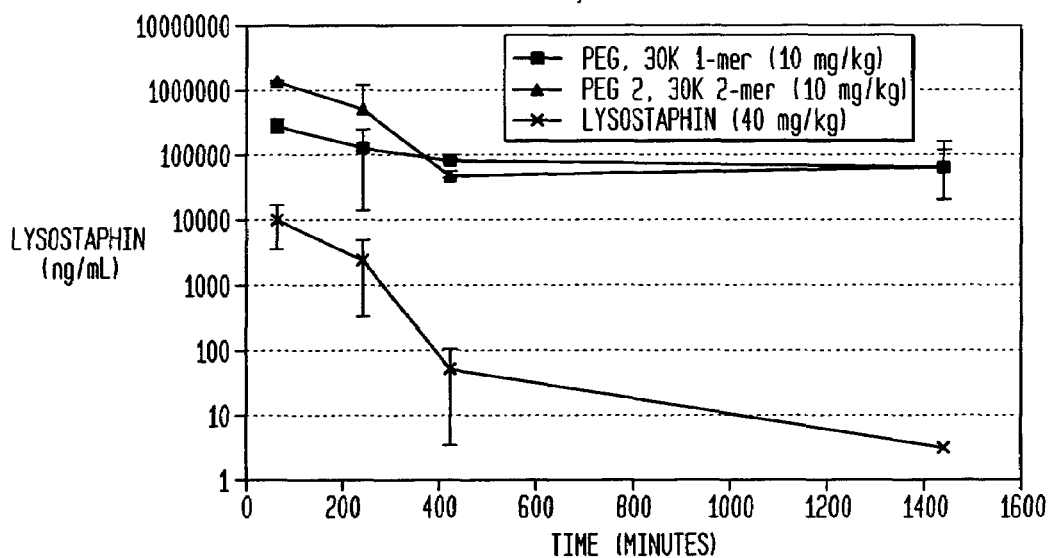
FIG. 12 depicts serum concentrations and half-life of lysostaphin conjugates according to another aspect of the present invention.

Serum Pharmacokinetics: Mice were injected with standard lysostaphin or PEGylated lysostaphin (30 k 1 and 2-mers) and the serum concentration was determined by ELISA over 24 hours. Higher serum concentrations are achieved with PEGylated enzyme and the half-life of the drug is dramatically increased. The 2-mer achieves higher peak serum lysostaphin concentrations but the long-term persistence seems comparable to that of the 1-mer (FIG. 12).

Figure 13:
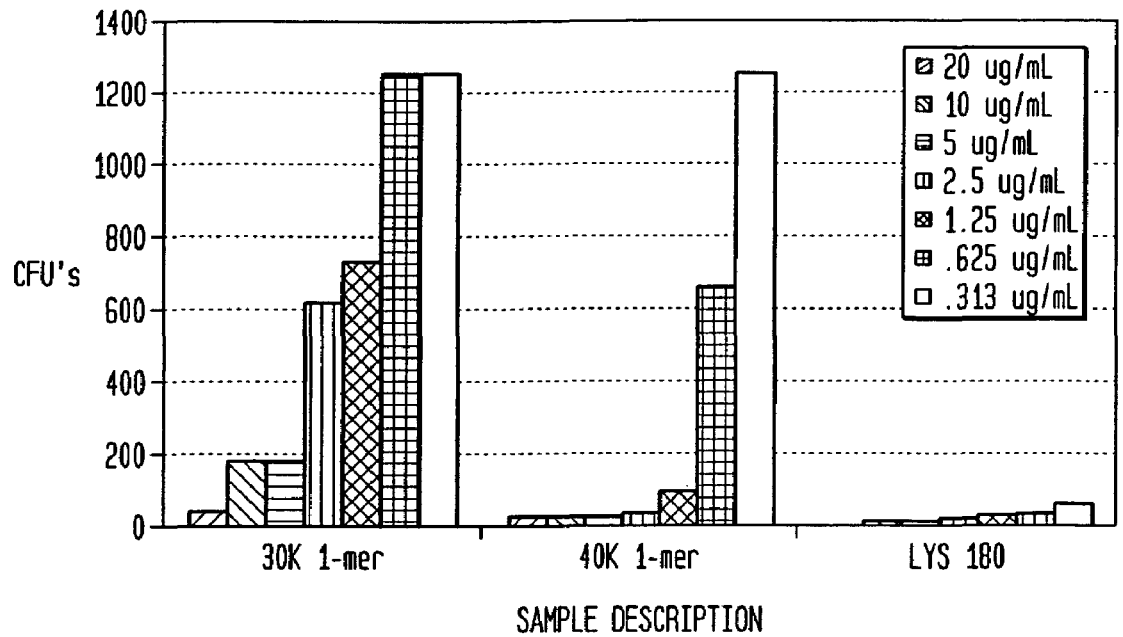
FIG. 13 compares the S. aureus type 5 killing activity in saline of two different molecular weight lysostaphin conjugates according to the present invention.

Killing Assay for Activity: The ability of lysostaphin 30 kD and 40 kD PEG 1-mers to kill SA in saline was tested with varying concentrations of the enzyme. The bacteria were streaked onto blood agar plates after a 1-2 hour incubation with lysostaphin and surviving colonies were counted the next day. The data is reported in FIG. 13 as surviving colonies of SA so that the lower value on the graph, the more effective the killing of SA by lysostaphin. The 40 k 1-mer has greater activity than the 30 k 1-mer, but both have significantly reduced activity compared to unconjugated lysostaphin.

Example 4

Recombinant Lysostaphin With A Terminal Cys For Polymer Conjugation

A lysostaphin construct, similar to lysostaphin was prepared except that it contained coding for the amino acids Ala-ala-Cys (in other words, similar to "mature" lysostaphin, but containing a terminal cysteine). The procedures described by Goodson et al., *Bio Technology*, 8, 343 (1990) and Benhar et al., *J. Biol Chem.*, 269, 13398 (1994) for the insertion of cysteine were followed.

Native lysostaphin does not contain any cysteines. Because the two alanines are un-important to the activity of lysostaphin, this portion of the enzyme could be modified without affecting activity. Thus, in order to conjugate lysostaphin with PEG in a defined and controlled manner, recombinant lysostaphin with a terminal ala-ala-cys was produced in *E. coli*.

Purification of Cysteine-containing Recombinant Lysostaphin

Cells from a 250 mL culture were harvested by centrifugation and frozen. They were thawed and lysed by extracting the pellet in 70 ml 0.1 M HCl. The extract was centrifuged at 4000 rpm and the supernatant dialyzed overnight at 4° C. against 4 liters PBS diluted 1:2 with water. The dialysate (approximately 150 mL) was further diluted to about 250 mL with water.

Prep 1. Approximately 200 mL of the crude solution was pumped onto a 1 ml SP Sepharose column (Pharmacia), equilibrated in 12.5 mM sodium phosphate, pH 7. After loading, the column was washed with the equilibration buffer and then eluted with 0.25 M NaCl in 12.5 mM sodium phosphate, pH 7. The eluant was concentrated using an Ultrafree 4 (10 kDa cutoff) device, (Millipore) to about 700 µL. Concentration was estimated by adsorbtion at 280 nm, following 1:20 dilution into PBS, using an extinction coefficient for lysostaphin of 0.49 mg/ml/OD 280:OD 280=0.201×20 ×0.49 mg/ml/OD 280=2.3 mg/ml. For 27 kDa, this corresponds to 85 µM lysostaphin if 100% pure, for a recovery of 0.7 mL×2.3 mg/mL, or 1.6 mg.

Prep 2. The remaining 50 mL was processed in a similar manner. The concentration of this material was determined as 1.18 mg/mL in a volume of 0.7 L. Recovery=0.82 mg. The total estimated recovery was 1.6+0.8 mg, or 2.4 mg.

Determination of Purity and Presence of Thiol

The free thiol (SH groups) of the recombinant lysostaphin were determined using DTNB (Ellman's reagent) and found to be 23.6 µM. Thus, at least 23.6/85=28% of the lysostaphin contains a free thiol, assuming no other proteins are contributing. SDS PAGE using 8-25% Phast gel (Pharmacia) indicated that a fraction was dimerized, further increasing the percentage of cysteine-lysostaphin obtained upon reduction of the dimer.

Labeling with iodoacetyl biotin, a reagent that reacts only with thiols confirmed that the recombinant lysostaphin contained a cysteine, unlike native lysostaphin. The cysteine can be reacted with reagents such as maleimide-PEG or iodoacetyl-PEG to conjugate lysostaphin at a unique site with PEG.

Example 5

NH$_2$ Terminal Lysostaphin PEGylation by Site-specific Oxidative Coupling

Lysostaphin has a threonine on its amino terminus. As has been described by Fields et al., *Biochem. J.*, 108, 883 (1968), Gaertner et al., *J. Biol. Chem.*, 269, 7224 (1994), and Geoghegan et al., *Bioconj. Chem.*, 3, 7224 (1992), amino terminus serine or threonine can be oxidized to a glyoxylyl derivative under mild conditions using sodium periodate. This group can then be reacted with amino-oxy PEG, hydrazide PEG or hydrazine PEG to yield lysostaphin pegylated on its amino terminus. An example of this reaction for the pegylation of IL-8 is described in Gaertner et al., *Bioconj. Chem.*, 7, 38 (1996).

Amino-oxy PEG (30 kD) is prepared as described in Gaertner et al., *Bioconjugate Chemistry* or purchased from Shearwater. Lysostaphin is prepared at 20 mg/mL in 1% NH$_4$(HCO$_3$), pH 8.3 and a 50-fold molar excess of methionine. A 10-fold molar excess of sodium periodate is added. After 10 min. at room temperature in the dark, the reaction is quenched by the addition of ¹/₂₀ volume 50% glycerol. The solution is then dialyzed in the dark against 0.1 M sodium acetate, pH 4.6. The solution of oxidized lysostaphin is adjusted to pH 3.6 with 1 N acetic acid, then reacted with a 5-fold molar excess of an amino-oxy PEG for 20 hr at room temp in the dark, with gentle stirring. Unreacted PEG is removed by ion exchange chromatography, followed by hydrophobic interaction chromatography to separate unconjugated lysostaphin.

The oxidized lysostaphin may also be functionalized with a reagent such as a (2-thio-pyridyl-cysteine hydrazide (Zara et al, *Anal. Biochem.*, 194, 156 (1991), which can then be reacted with a thiol reactive PEG such as PEG-maleimide.

Figure 14:
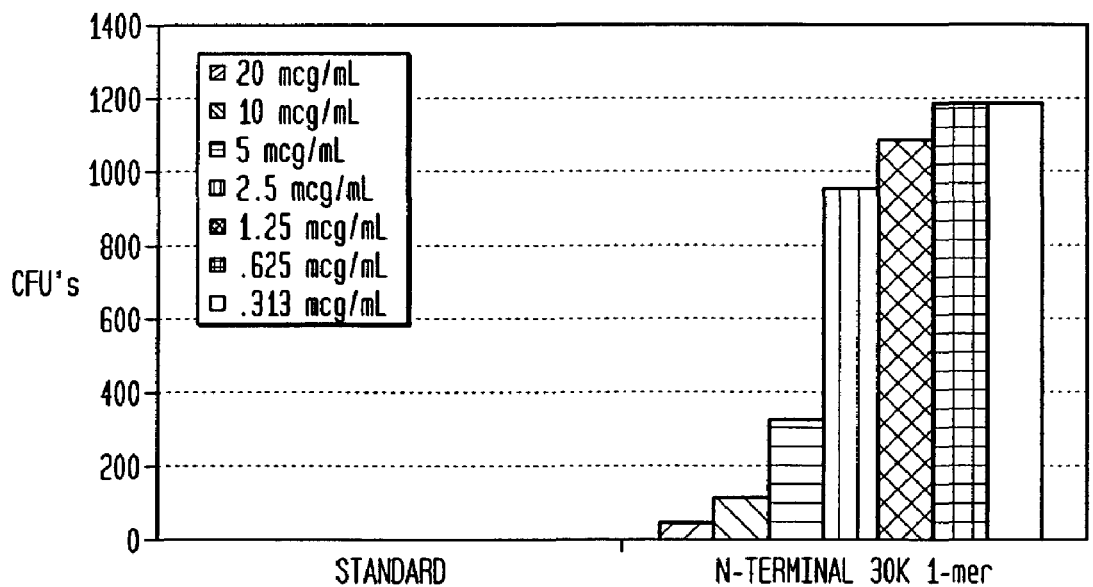
FIG. 14 depicts the S. aureus type 5 killing activity in saline of a lysostaphin conjugate according to yet another aspect of the present invention.

Killing Assay for Activity: The ability of the N-terminal 30 kD PEGlyated lysostaphin to kill SA in saline was tested with varying concentrations of the enzyme. The bacteria were streaked onto blood agar plates after a 1-2 hour incubation with lysostaphin and surviving colonies were counted the next day. The data is reported in FIG. 14 as surviving colonies of SA so that the lower value on the graph, the more effective the killing of SA by lysostaphin. The N-terminal 30k 1-mer has activity but not at a greater level than previously tested 1-mers (either 30k or 40 K).

Examples 6 to 8

PEGylation Using Two-step Heteroligation

Heteroligation chemistry involves labeling component A (in this case lysostaphin) with a reactive group that is capable of reacting only with the reactive group present on component B (in this case, a PEG). In this Example, lysostaphin is chemically modified on a lysine amino groups with a thiol group and then reacted with an electrophilic PEG reagent (e.g., PEG-maleimide), as compared to Example 4, wherein lysostaphin is genetically modified to insert a cysteine group, (which contains a reactive thiol group). Heteroligation chemistry is described in above-referenced *Bioconjugate Chemistry*.

Lysostaphin was prepared at 20 mg/mL in 75 mM HEPES+2 mM EDTA, pH 7.5 buffer and N-succinimidyl 3-[2-pyridylidithio]propionate (SPDP) (0.1M in DMF) was added dropwise while mixing. The molar ratio of SPDP to lysostaphin was varied in order to vary the degree of labeling. After 1 hr, the pH was reduced by the addition of ¹/₁₀ volume 1 M sodium acetate, pH 5 and adjusted to pH 5 with 1 N HCl. The solution was made 25 mM by the addition of solid dithiothreitol (DTT). After 15 min., the solution was dialyzed overnight into 10 mM sodium acetate, 2 mM EDTA, pH 5 at 4° C. to remove the DTT. The extent of labeling was determined by the use of DTNB (Ellman's reagent) and from the molar concentration determined by adsorbance, at 280 nm using an extinction coefficient of 0.49 mg/ml per absorbance unit at 280 nm.

The thiolated lysostaphin was then reacted with the electrophilic, thiol-selective mPEG-vinylsulfone (Shearwater M-VS-5000), mPEG-maleimide (Shearwater M-MAL-5000) and mPEG-orthopyridyl disulfide (Shearwater M-OPSS-5000). A haloacyl PEG would also be suitable. The reactions were performed at appropriate pH for the PEG reagents to be selective for the thiol. For example, the vinylsulfone addition was performed about pH 7-8. The maleimde addition and disulfide exchange were at performed at pH 6-7.

Excess PEG was removed by ion exchange chromatography. Hydrophobic chromatography could also be used. Lysostaphin containing varying amounts of PEG was thereby fractionated.

The advantages of the two-step method include the ability to limit or control the extent of PEGylation. Additionally, a long chain thiolating reagent can be used (e.g., LC-SPDP, Pierce, #21651). These reagents allow the thiol group to extend further beyond the protein surface and facilitate conjugation to bulky molecules such as PEG.

A further advantage of the above two-step method is that the thiol will remain reactive for extended periods of time, especially in the absence of oxygen, in EDTA containing buffers and under acidic conditions, all of which minimize oxidation. Likewise, the PEGS described above are all stable at a pH where the reagents are reactive with thiols. This is in contrast to the NHS-ester PEGS which require alkaline conditions to react with amino groups. NHS esters are not stable in base.

Bulky reagents generally react more slowly than small reagents. By employing the two step heteroligation method described in this example, the reaction may be allowed to proceed for an extended period of time and allow for more efficient coupling. This permits less of the PEG reagent to be used, reducing costs. Furthermore, because a higher percentage of the PEG is coupled, purification of the desired PEG-lysostaphin conjugate may be facilitated. These advantages are also present in Example 4.

The methods described in Examples 1-8 can be extended to other anti-microbial proteins, such as nisin. A terminal cysteine can be engineered into a protein as in Example 4, and then coupled to PEG as described in Examples 6 to 8.

As will be readily appreciated, numerous variations of and combinations of the features set forth above can be utilized without departing from the present invention as set forth in the claims. Such variations are not regarded as a departure from the spirit and scope of the invention, and al such modifications are intended to be included within the scope of the following claims.

What is claimed is:

1. A composition comprising polyethylene glycol (PEG) conjugated to lysostaphin, wherein said conjugate is a fractionated conjugate consisting essentially of a fraction of lysostaphin conjugated to a single PEG molecule, wherein said lysostaphin retains antimicrobial activity capable of killing live *Staphylococcus aureus* type 5 in an in vitro killing assay.

2. The composition of claim 1, wherein said lysostaphin conjugated to said polyethylene glycol has a longer in-vivo half-life than non-conjugated lysostaphin.

3. The composition of claim 1, wherein said lysostaphin is capable of cleaving cross-linked polyglycine bridges in the cell wall peptidoglycan of staphylococci.

4. The composition of claim 1, wherein conjugating said lysostaphin to said polyethylene glycol permits a greater serum concentration of lysostaphin than is achievable for non-conjugated lysostaphin.

5. The composition of claim 1, wherein said lysostaphin is a recombinant lysostaphin.

6. The composition of claim 1, wherein said lysostaphin is naturally derived.

7. The composition of claim 6, wherein said recombinant lysostaphin possesses a terminal cysteine.

8. The composition of claim 1, wherein said PEG is straight-chained.

9. The composition of claim 1, wherein said PEG is branched.

10. The composition of claim 1, wherein said lysostaphin conjugated to PEG remains active for a longer period of time than in the absence of conjugation to said PEG.

11. The composition of claim 1, wherein said lysostaphin conjugated to PEG is provided in dosage form for administration of 1 to 40 mg/kg/day to a subject.

12. The composition of claim 1, wherein said fractionated conjugate consisting essentially of a fraction of lysostaphin conjugated to a single PEG molecule is greater than 99% pure.

13. The composition of claim 1, wherein said PEG is 30 kD.

14. A pharmaceutical composition for treating microbial infection comprising polyethylene glycol (PEG) conjugated to lysostaphin, wherein said conjugate is a fractionated conjugate consisting essentially of a fraction of lysostaphin conjugated to a single PEG molecule, wherein said lysostaphin retains antimicrobial activity capable of killing live *Staphylococcus aureus* type 5 in an in vitro killing assay, and a pharmaceutically acceptable carder.

15. The pharmaceutical composition of claim 14, wherein said lysostaphin conjugated to said polymer is less immunogenic than non-conjugated lysostaphin.

16. The pharmaceutical composition of claim 14, wherein said lysostaphin conjugated to said polymer has a greater half-life and serum concentration than non-conjugated lysostaphin.

17. The pharmaceutical composition of claim 14, wherein said lysostaphin is capable of cleaving the cross-linked polyglycine bridges in the cell wall peptidoglycan of staphylococci.

18. The pharmaceutical composition of claim 14, further comprising a non-conjugated antibacterial enzyme.

19. The pharmaceutical composition of claim 18, wherein said non-conjugated antibacterial enzyme is selected from the group consisting of lysostaphin, lysostaphin analogue, lysozyme, mutanolysin, cellozyl muramidase, and combinations thereof.

20. The pharmaceutical composition of claim 14, further comprising an antibiotic.

21. The pharmaceutical composition of claim 20, wherein said antibiotic is selected from the group consisting of β-lactams, cephalosporins, aminoglycosides, sulfonamides, antifolates, macrolides, quinolones, glycopeptides, polypeptides and combinations thereof.

22. A method for the prophylactic or therapeutic treatment of a microbial infection in a mammal comprising administering to said mammal a pharmaceutical composition comprising polyethylene glycol (PEG) conjugated to lysostaphin, wherein said conjugate is a fractionated conjugate consisting essentially of a fraction of lysostaphin conjugated to a single PEG molecule, wherein said lysostaphin retains antimicrobial activity capable of killing live *Staphylococcus aureus* type 5 in an in vitro killing assay, and a pharmaceutically acceptable carrier, in an amount effective for preventing or treating said infection.

23. The method of claim 22, wherein said infection is a bacterial infection.

24. The method of claim 23, wherein said bacterial infection is caused by bacteria from the genus *Staphylococcus*.

25. The method of claim 24, wherein said bacteria comprise *Staphylococcus aureus*.

26. The method of claim 24, wherein said bacteria comprise *Staphylococcus epidermidis*.

* * * * *